(12) United States Patent
Krzysik et al.

(10) Patent No.: US 7,547,443 B2
(45) Date of Patent: Jun. 16, 2009

(54) SKIN CARE TOPICAL OINTMENT

(75) Inventors: Duane G. Krzysik, Appleton, WI (US); Stephen Baldwin, Menasha, WI (US); Bozena Nogaj, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 615 days.

(21) Appl. No.: 10/659,967

(22) Filed: Sep. 11, 2003

(65) Prior Publication Data
US 2005/0058669 A1 Mar. 17, 2005

(51) Int. Cl.
A61K 6/00 (2006.01)
(52) U.S. Cl. ..................................................... 424/401
(58) Field of Classification Search ................. 424/401, 424/489
See application file for complete search history.

(56) References Cited

U.S. PATENT DOCUMENTS

| | | | |
|---|---|---|---|
| 3,301,746 A | 1/1967 | Sanford et al. | |
| 3,812,000 A | 5/1974 | Salvucci et al. | |
| 3,814,096 A | 6/1974 | Weiss et al. | |
| 3,896,807 A | 7/1975 | Buchalter | |
| 3,974,025 A | 8/1976 | Ayers | |
| 4,112,167 A | 9/1978 | Dake et al. | |
| 4,191,609 A | 3/1980 | Trokhan | |
| 4,208,459 A | 6/1980 | Becker et al. | |
| 4,300,981 A | 11/1981 | Carstens | |
| 4,637,859 A | 1/1987 | Trokhan | |
| 4,690,821 A | 9/1987 | Smith et al. | |
| 4,798,603 A | 1/1989 | Meyer et al. | |
| 4,962,133 A | 10/1990 | Chromecek et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,221,534 A | 6/1993 | DesLauriers et al. | |
| 5,509,915 A | 4/1996 | Hanson et al. | |
| 5,520,917 A * | 5/1996 | Mizuguchi et al. | 424/401 |
| 5,525,345 A | 6/1996 | Warner et al. | |
| 5,612,045 A | 3/1997 | Syverson | |
| 5,624,676 A | 4/1997 | Mackey et al. | |
| 5,705,164 A | 1/1998 | Mackey et al. | |
| 5,716,692 A | 2/1998 | Warner et al. | |
| 5,720,966 A | 2/1998 | Ostendorf | |
| 5,843,056 A | 12/1998 | Good et al. | |
| 5,855,999 A | 1/1999 | McCormack | |
| 5,879,341 A | 3/1999 | Odorzynski et al. | |
| 6,063,335 A | 5/2000 | Pirolo et al. | |
| 6,146,648 A | 11/2000 | Bret et al. | |
| 6,149,934 A * | 11/2000 | Krzysik et al. | 424/443 |
| 6,179,961 B1 | 1/2001 | Ficke et al. | |
| 6,211,139 B1 | 4/2001 | Keys et al. | |
| 6,217,890 B1 * | 4/2001 | Paul et al. | 424/402 |
| 6,238,682 B1 | 5/2001 | Klofta et al. | |
| 6,261,580 B1 | 7/2001 | Lehrter et al. | |
| 6,287,581 B1 * | 9/2001 | Krzysik et al. | 424/402 |
| 6,340,467 B1 * | 1/2002 | Morrison | 424/405 |
| 6,410,039 B1 | 6/2002 | Walker | |
| 6,428,794 B1 | 8/2002 | Klofta et al. | |
| 6,433,068 B1 | 8/2002 | Morrison et al. | |
| 6,458,343 B1 | 10/2002 | Zeman et al. | |
| 6,503,412 B1 | 1/2003 | Schroeder | |
| 6,503,526 B1 | 1/2003 | Krzysik et al. | |
| 6,534,074 B2 | 3/2003 | Krzysik et al. | |
| 6,570,054 B1 | 5/2003 | Gatto et al. | |
| 6,586,652 B1 | 7/2003 | Roe et al. | |
| 6,627,787 B1 | 9/2003 | Roe et al. | |
| 6,716,204 B1 | 4/2004 | D'Acchioli et al. | |
| 6,733,772 B1 | 5/2004 | Bret et al. | |
| 6,825,393 B2 | 11/2004 | Roe et al. | |
| 2001/0014350 A1 | 8/2001 | Krzysik et al. | |
| 2002/0128615 A1 | 9/2002 | Tyrrell et al. | |
| 2002/0128621 A1 | 9/2002 | Kruchoski et al. | |
| 2002/0136755 A1 | 9/2002 | Tyrrell et al. | |
| 2002/0165508 A1 | 11/2002 | Klofta et al. | |
| 2005/0058669 A1 | 3/2005 | Krzysik et al. | |

FOREIGN PATENT DOCUMENTS

| | | | |
|---|---|---|---|
| EP | 0497144 | * | 1/1992 |
| WO | WO 92/16216 A1 | | 10/1992 |
| WO | WO 99/45973 A1 | | 9/1999 |
| WO | WO 00/64407 A1 | | 11/2000 |
| WO | WO 00/64502 A1 | | 11/2000 |
| WO | WO 00/64503 A1 | | 11/2000 |
| WO | WO 00/69484 A1 | | 11/2000 |
| WO | WO 02/05789 A2 | | 1/2002 |
| WO | WO 02/34305 A2 | | 5/2002 |
| WO | WO 03/004070 A1 | | 1/2003 |
| WO | WO 03/005981 A2 | | 1/2003 |
| WO | WO 03/028776 A1 | | 4/2003 |
| WO | WO 03/037292 A1 | | 5/2003 |
| WO | WO 03/039492 A1 | | 5/2003 |
| WO | WO 2004/087092 A1 | | 10/2004 |

OTHER PUBLICATIONS

Gels, Internet article, http://www.penreco.com/products/gels/gels.asp, last checked Aug. 10, 2004.
International Search Report from PCT/US2004/011595 dated Sep. 1, 2004.
Flick, E.W., "Cosmetic and toiletry formulations," 1984, p. 37, 154, Noyes Publications, XP002303389.
International Search Report from PCT/US2004/017636 dated Nov. 17, 2004.
International Search Report from PCT/US2004/019447 dated Feb. 21, 2005.

* cited by examiner

*Primary Examiner*—Humera N Sheikh
(74) *Attorney, Agent, or Firm*—Armstrong Teasdale LLP

(57) ABSTRACT

Topical ointment for preventing and treating diaper rash are disclosed. The topical ointments comprise an emollient, a structurant, a rheology enhancer, and other optional components. In one preferred embodiment, the topical ointment comprises a particulate material such as zinc oxide as an optional component.

6 Claims, No Drawings

SKIN CARE TOPICAL OINTMENT

BACKGROUND OF THE INVENTION

The present invention relates to formulations that may be topically applied to the skin to improve skin health. More particularly, the present invention relates to a topical ointment that can be applied directly to skin, or applied to an absorbent article to be used next to the skin, comprising an emollient, a structurant, and a rheology enhancer. The novel topical ointment has improved spreadability over the skin, enhanced aesthetics, and provides improved film formation properties to block water borne irritants from entering the skin.

Diaper rash and related skin problems are common forms of skin irritation and inflammation of those parts of an infant's or adult's body normally covered by an absorbent product such as a diaper or incontinence garment. Also, the skin irritation may be seen in areas adjacent the covered skin. This skin condition may also be commonly referred to as diaper dermatitis, napkin dermatitis, napkin rash, and nappy rash.

Although the precise number of infants who suffer from diaper rash is unknown, it is believed to be substantial. Further, while certainly more common in infants, this condition is not limited solely to infants. Any individual who suffers from incontinence may also develop this type of dermatitis. This includes both the elderly, critically ill, and non-ambulatory individuals. Symptoms from this type of dermatitis can range from moderate to very severe.

It is believed that the principal cause of diaper dermatitis is the holding of urine and/or feces against the skin. With urine, urea contained therein is broken down into ammonium hydroxide by the ureases, which leads to an increase in pH on the skin's surface. When the pH becomes basic on the skin's surface, numerous enzymes may be activated and interfere with several naturally occurring skin components.

Conventional methods for combating diaper rash have been diverse. Several methods have included an attempt to minimize the contact of the skin with feces or urine present in a soiled diaper. Typically, an artificial barrier is employed to accomplish this. There have also been further attempts directed toward counteracting other suspected causes of diaper rash by promoting dryness in the diapered area, and preventing microbial growth and inflammation with conventional agents. Such a strategy includes frequent diaper changing, reduced use of plastic pants, triple diapering, and careful washing and sterilization of diapers.

Most commonly, parents have attempted to control diaper rash through the use of a topical ointment, which acts as an occlusive, barrier-type layer. Such ointments typically comprise petrolatum and/or mineral oil in combination with a wax and a small amount of additives, such as zinc oxide, to provide the desired protection. Most conventional topical ointments available have been in the form of a water-in-oil emulsion. The high viscosity associated with these products keeps the diaper rash ointment from being substantially washed off of the skin by urine and/or feces. In many cases, the high viscosity of the ointment is the result of the inclusion of zinc oxide, or another particulate, as a component. When the ointment is applied to skin, urine and/or feces are repelled away from the ointment, and hence away from the skin.

Although conventional topical ointments have been somewhat satisfactory in combating various skin ailments including diaper dermatitis, many of the ointments do not spread easily or evenly across the skin surface, and may feel greasy or gritty upon application to the skin. Also, some conventional formulations have been less than satisfactory in their ability to uniformly suspend particulate materials such as clays, pigments, talc, microcapsules, microsponges, polymer entrapment particles or skin health actives in the formulation, which results in an uneven application of the particulate onto the skin. As such, there is a need for improved topical ointments for use on the skin, which can evenly distribute particles or other skin health actives to prevent or minimize diaper dermatitis and related skin disorders.

SUMMARY OF THE INVENTION

The present invention relates to topical ointments for direct application to the skin for preventing and treating diaper dermatitis and related rashes and skin ailments. In one embodiment, the topical ointments can be applied directly onto an absorbent product, such as a diaper or incontinence garment, such that upon use of the product, the ointment is transferred to the skin of the wearer and provides a benefit in reducing diaper dermatitis.

In order to ensure that any particulate materials present in the topical ointment are evenly suspended therein after processing and introduction into a container, the topical ointments have a process temperature viscosity as defined herein of from about 50 cPs to about 50,000 cPs.

Specifically, the topical ointments comprise the following components:
  (a) an emollient;
  (b) a structurant;
  (c) a rheology enhancer; and
  (d) other optional components.

Other optional components suitable for use in the topical ointments described herein include, for example, particulate materials, low HLB surfactants, (water-in-oil emulsifiers), anti-inflammatories, antibiotics, anti-fungals, anti-histamines, moisturizers, vitamins, botanical extracts, skin protectants, astringents, lipids, sterols, powders, fragrances, antioxidants, colorants, microcapsules, microsponges, polymeric entrapment particles, preservatives, fragrances, optical brighteners, sunscreens, alpha hydroxy acids, and combinations thereof.

Briefly, therefore, the present invention is directed to a topical ointment comprising from about 10% (by total weight of the ointment) to about 89% (by total weight of the ointment) of an emollient, from about 10% (by total weight of the ointment) to about 50% (by total weight of the ointment) of a structurant, and from about 0.1% (by total weight of the ointment) to about 40% (by total weight of the ointment) of a rheology enhancer.

The present invention is further directed to a topical ointment comprising from about 10% (by total weight of the ointment) to about 89% (by total weight of the ointment) of an emollient, from about 10% (by total weight of the ointment) to about 50% (by total weight of the ointment) of a structurant, from about 0.1% (by total weight of the ointment) to about 40% (by total weight of the ointment) of a rheology enhancer, from about 0.1% (by total weight of the ointment) to about 25% (by total weight of the ointment) of a particulate material, and from about 0.1% (by total weight of the ointment) to about 10% (by total weight of the ointment) of a low HLB surfactant.

Other features and advantages of this invention will be in part apparent and in part pointed out hereinafter.

DETAILED DESCRIPTION OF THE PREFERRED EMBODIMENTS

In accordance with the present invention, it has been discovered that various types of rheology enhancers can be introduced into a topical ointment for preventing and treating diaper rash to improve various properties of the topical ointment. Surprisingly, the rheology enhancers result in improved spreadability of the ointment across the surface of the skin, and provide enhanced aesthetics of the ointment. Additionally, the rheology enhancers result in improved film formation properties, which result in a blocking of water borne irritants from entering the skin.

The topical ointments described herein are suitable for preventing and treating diaper rash and other related skin ailments and diseases including eczema, dermatitis, and allergic skin reactions. The topical ointments are effective in treating such skin conditions as cracking, chaffing, and redness, and are particularly suited for restoring the skin to its natural healthy condition. The topical ointments may suitably be applied directly to the skin. Once applied to the skin, the topical ointment provides a barrier layer between the skin and potential skin irritants, such as urine and feces. Because the topical ointments are viscous materials, they do not wash away from the skin easily after urination and/or defecation and provide a substantial barrier layer.

Along with being suitably applied directly to the skin, the topical ointments described herein may also be applied directly onto an absorbent article, such as a diaper or incontinence garment. Typically, the topical ointment is applied to the absorbent article in the crotch and/or buttock-contacting area of the article as these areas on the wearer are most susceptible to diaper rash. When the absorbent article is then worn, the topical ointment can transfer from the article to the wearer's skin where it forms a barrier layer protecting the skin from irritants that can ultimately lead to diaper rash and other skin conditions. Further, the topical ointment can be applied both directly to the skin and to an absorbent article to ensure a sufficient amount is on the skin after urination and/or defecation.

The topical ointments described herein are either solid or semi-solid at room temperature, and are easily spreadable over the skin in the form of a cream, salve, jelly, stick, or other commercially acceptable form. As used herein, the term "semi-solid" means that the topical ointment has a rheology typical of pseudoplastic or plastic fluids. When applied to the skin or absorbent product, the topical ointments described herein impart a soft, lubricious, lotion-like feel to the touch.

As noted above, the topical ointments of the present invention comprise an emollient, a structurant, and a rheology enhancer. Other optional components, such as particulate materials, low HLB surfactants, and others may also be included in the topical ointments as discussed herein to impart additional benefits to the topical ointment.

An emollient is an active ingredient in a formulation that typically softens, soothes, supples, coats, lubricates and/or moisturizes the skin. Generally, emollients accomplish several of these objectives simultaneously. Typically, emollients suitable for use in the topical ointments described herein are fluids at room temperature such that they impart a soft, lubricious lotion-like feel upon use. The emollient is present in the topical ointment in an amount of from about 10% (by total weight of the ointment) to about 89% (by total weight of the ointment), more desirably from about 30% (by total weight of the ointment) to about 80% (by total weight of the ointment), and still more desirably from about 60% (by total weight of the ointment) to about 80% (by total weight of the ointment).

Suitable emollients for use in the topical ointments of the present invention are typically substantially water free. Although the emollient may contain trace amounts of water as a contaminant without substantially harming the topical ointment, it is preferred that the amount of water be less than about 5% by weight of the emollient component of the topical ointment to reduce the likelihood of microbial growth and product destruction.

Suitable emollients for use in the topical ointments of the present invention include, for example, petrolatum, mineral oil, mineral jelly, isoparaffins, vegetable oils such as avocado oil, borage oil, canola oil, castor oil, chamomile, coconut oil, corn oil, cottonseed oil, evening primrose oil, safflower oil, sunflower oil, soybean oil, sweet almond, and the like, sterols and derivates, lanolin, partially hydrogenated vegetable oils, polydimethylsiloxanes such as methicone, cyclomethicone, dimethicone, dimethiconol, and trimethicone, organo-siloxanes (i.e., where the organic functionality can be selected from alkyl, phenyl, amine, polyethylene glycol, amine-glycol, alkylaryl, carboxal, and the like), silicone elastomer, gums, resins, fatty acid esters (esters of $C_6$-$C_{28}$ fatty acids and $C_6$-$C_{28}$ fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, Guerbet alcohols, Guerbet Acids, Guerbet Esters, and other cosmetically acceptable emollients.

Additionally, some emollients are solids at room temperature, and may have a dual benefit of being solid emollients (at room temperature) as well as structuring agents. Compounds that act as both emollients and structuring agents include, for example, $C_{14}$-$C_{28}$ fatty acid esters (esters of $C_{12}$-$C_{28}$ fatty acids and $C_{12}$-$C_{28}$ fatty alcohols), $C_{14}$-$C_{28}$ fatty alcohols, $C_{14}$-$C_{28}$ fatty acids, $C_{14}$-$C_{28}$ fatty acid ethoxylates, $C_{14}$-$C_{28}$ fatty ethers and $C_{16}$-$C_{30}$ alkyl siloxanes.

The structurant utilized in the topical ointments described herein help to solidify the emollient and other components into a solid or semi-solid cream or paste. The structurant is present in the topical ointment in an amount of from about 10% (by total weight of the ointment) to about 50% (by total weight of the ointment), desirably from about 20% (by total weight of the ointment) to about 40% (by total weight of the ointment).

Suitable structurants for use in the topical ointments disclosed herein have a melting point of about 45° C. to about 85° C. and may include, for example, waxes including animal waxes, vegetable waxes, mineral waxes, synthetic waxes, and polymers. Exemplary waxes include bayberry wax, beeswax, stearyl dimethicone, stearyl trimethicone, $C_{20}$-$C_{22}$ dimethicone, $C_{20}$-$C_{22}$ trimethicone, $C_{24}$-$C_{28}$ dimethicone, $C_{20}$-$C_{22}$ trimethicone, $C_{30}$ alkyl dimethicone, candelilla wax, carnauba, ceresin, cetyl esters, stearyl benzoate, behenyl benzoate, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acide wax, motan wax, ouricury wax, ozokerite parrafin, PEG-6 beeswax, PEG-8 beeswax, rezowax, rice bran wax, shellac wax, spent grain wax, spermaceti wax, synthetic spermaceti wax, synthetic beeswax, synthetic candelilla wax, synthetic carnuba wax, synthetic japan wax, synthetic jojoba wax, $C_{14}$-$C_{28}$ fatty acid ethoxylates and $C_{14}$-$C_{28}$ fatty ethers, $C_{14}$-$C_{28}$ fatty alcohols, $C_{14}$-$C_{28}$ fatty acids, polyethylene, oxidized polyethylene, ethylene-alpha olefin copolymers, ethylene homopolymers such as Petrolite EP copolymers from Baker Hughes Inc., (Sugar Land Tex.), $C_{18}$-$C_{45}$ olefins, poly alpha olefins such as Vybar Polymers from Baker Hughes Inc. or Okerin Polymers from Honeywell Specialty Chemicals, (Duluth, Ga.), hydrogenated vegetable oils, polyhydroxy fatty acid esters, polyhydroxy fatty acid amides, ethoxylated fatty alcohols and esters of $C_{12}$-$C_{28}$ fatty acids, and $C_{12}$-$C_{28}$ fatty alcohols.

The rheology enhancers present in the topical ointments impart numerous desirable characteristics and properties to the ointments. First, the rheology enhancers help the topical ointments to maintain a high viscosity at elevated temperatures, such as those encountered during storage and transportation as well as during cooling of the product. Desirably, the rheology enhancer increases the viscosity of the lubricating formulation by at least about 50%, more desirably at least about 500%, and even more desirably at least about 1000%. This helps ensure that the topical ointments do not substantially separate out during processing, storage, and transportation. Additionally, the rheology enhancers impart excellent spreadability characteristics to the topical ointments such that the ointment is easily spreadable across the skin evenly and efficiently. This allows a user to easily introduce an even coating of the ointment onto the skin and assures that there will be no bare spots on the treated skin that could be susceptible to urine and/or feces contact, which can result in diaper rash. Also, the rheology enhancer provides the ointment with an improved film formation property such that water borne irritants are blocked from entering the skin when present at or near the skin surface. Further, the rheology enhancers have the ability to uniformly suspend particulate materials, such as zinc oxide, titanium dioxide, microcapsules, or microsponges, in the formulation. This uniform suspension of particulate materials, which can provide additional skin health benefits, ensures an even application of the particulate materials on the skin during the application of the topical ointment.

The rheology enhancer is present in the topical ointment in an amount of from about 0.1% (by total weight of the ointment) to about 40% (by total weight of the ointment), desirably from about 0.5% (by total weight of the ointment) to about 30% (by total weight of the ointment) and even more desirably from about 1% (by total weight of the ointment) to about 25% (by total weight of the ointment).

Suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha olefins and isobutene, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blend from Penreco) are particularly preferred. Also, Vistanex (Exxon) and Presperse (Amoco) polymers are particularly suitable rheology enhancers.

The topical ointments described herein have a specific process temperature viscosity, as defined herein. The process temperature viscosities defined herein for the topical ointments allow the ointments to keep suspended various particles in the ointment during the cooling of the ointment in the container after processing. This is important as it is advantageous for the particles to be evenly suspended throughout the product when utilized by the consumer, which is after the product has cooled in the container.

The topical ointments described herein have a process temperature viscosity of from about 50 cPs to about 50,000 cPs, desirably from about 75 cPs to about 10,000 cPs, and more desirably from about 80 cPs to about 5,000 cPs. The process temperature is typically from about 5° C. to about 20° C. above the melting point of the topical ointment.

In addition to the emollient, structurant, and rheology enhancer, the topical ointments described herein may also comprise a particulate material, which can impart additional benefits to the skin upon application. As used herein, particulate material is meant to include a dry, particulate material having a size of from about 0.001 micrometers to about 150 micrometers, desirably from about 0.01 micrometers to about 100 micrometers, and still more desirably from about 0.1 micrometers to about 30 micrometers. The particulate materials may be colored or non-colored, and may provide one or more benefits to the topical ointments or skin such as, for example, coloration, light diffraction, oil absorption, translucency, opacification, pearlescence, matte appearance, lubricious feel, skin coverage, and the like. Typically, the particulate material may be present in the topical ointment in an amount of from about 0.1% (by total weight of the ointment) to about 35% (by total weight of the ointment).

Suitable particulate materials include various organic and inorganic pigments that color the composition or the skin upon use. Organic pigments are generally various types including azo, indigold, triphenylmethane, anthraquinone, and xanthine dyes, which are designated as D&C and FD&C blues, browns, greens, oranges, reds, yellows, etc. Inorganic pigments are generally insoluble metallic salts of certified color additives referred to as lakes or iron oxides. Suitable pigments include, for example, red iron oxide, yellow iron oxide, black iron oxide, brown iron oxide, ultramarine, FD&C Red, Nos. 2, 5, 6, 7, 10, 11, 12, 13, 30 and 34, FD&C Yellow No. 5, Red 3, 21, 27, 28, and 33 Aluminum Lakes, Yellow 5, 6, and 10 Aluminum Lakes, Orange 5 Aluminum Lake, Blue 1 Aluminum Lake, Red 6 Barium Lake, Red 7 Calcium Lake, and the like. Other useful particulate materials include talc, mica, titanated mica (mica coated with titanium dioxide), iron oxide titanated mica, magnesium carbonate, calcium carbonate, magnesium silicate, silica (including spherical silica, hydrated silica, and silica beads), titanium dioxide, zinc oxide, nylon powder, polyethylene powder, ethylene acrylates copolymer powder, methacrylate powder, polystyrene powder, silk powder, crystalline cellulose, starch, bismuth oxychloride, guanine, kaolin, bentonite, hectorite, laponite, chalk, diatomaceous earth, microsponges, microcapsules, boron nitride, and the like.

Along with the components described above, an optional low HLB (hydrophilic/lipophilic balance) surfactant can be added to the topical ointment which is capable of emulsifying or dispersing one or more components in the topical ointment. Desirably, the low HLB surfactant has an HLB in the range of from about 2 to about 7. The amount of low HLB surfactant can be from about 0.1% (by total weight of the ointment) to about 20% (by total weight of the ointment), more desirably from about 0.1% (by total weight of the ointment) to about 10% (by total weight of the ointment). Low HLB surfactants are employed typically to form emulsions or dispersions of various components.

Suitable surfactants for use in the topical ointments include, for example, sorbitan monooleate, sorbitan sequioleate, sorbitan trioleate, glyceryl stearate, sorbitan stearate, sorbitan tristearate, and the like, as well as mixtures thereof.

In addition to the components described above, the topical ointments described herein may additionally comprise a hydrophilic skin care active to impart a skin care benefit to the ointment. The skin care active may be present in the ointment in an amount of from about 0.1% (by total weight of ointment) to about 10% (by total weight of the ointment). Suitable skin care actives include, for example, botanicals, glycerin, hydrogenated starch hydrolysate, propylene glycol, sodium PCA, sodium lactate, sorbitol, and mixtures thereof.

In order to better enhance the benefits to consumers, additional ingredients can be incorporated into the lubrication formulation described herein. The classes of ingredients and their corresponding benefits include, without limitation: antifoaming agents (reduce the tendency of foaming during processing); antimicrobial actives; antivirul actives: antifungal actives; antiseptic actives; antioxidants (product integrity to prevent oxidation of natural oils and other ingredients on the formulation or composition); astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product including vitamins); colorants (impart color to the product); deodorants (reduce or eliminate unpleasant odor and protect against the formation of malodor on body surfaces); film formers (to hold active ingredients on the skin by producing a continuous film on skin upon drying); fragrances (consumer appeal); lubricants, such as silicones and organomodified silicones; natural moisturizing agents (NMF) and other skin moisturizing ingredients known in the art; skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); solvents (liquids employed to dissolve components found useful in the cosmetics or drugs); and UV absorbers.

EXAMPLE 1

In this Example, several topical ointments were prepared and evaluated for viscosity at 55° C. (1/sec) and viscosity at 60° C. (1/sec). The composition of each of the topical ointments tested are set forth in the tables below, along with the viscosity results.

TABLE 1

| Component | A Wt. % | B Wt. % | C Wt. % | D Wt. % |
|---|---|---|---|---|
| Petrolatum | 76.00 | 78.00 | 76.00 | 83.00 |
| Alpha Olefin Polymer ($C_{24}$-$C_{28}$) | 12.00 | 7.00 | 3.00 | 3.00 |
| Ethylene/Vinyl Acetate Copolymer with Polyethylene | 12.00 | 15.00 | 18.00 | 12.00 |
| Viscosity @ 55° C. 0.5 1/sec | 17,100 | 23,000 | 63,500 | 10,200 |
| Viscosity @ 60° C., 0.5 1/sec | 171 | 206 | 2990 | 1670 |

TABLE 2

| Component | A Wt. % | B Wt. % | C Wt. % | D Wt. % | E Wt. % | F Wt. % |
|---|---|---|---|---|---|---|
| Petrolatum | 80.00 | 80.00 | 78.00 | 77.00 | 80.00 | 79.00 |
| Polyethylene and Ethylene/Vinyl Acetate Copolymer | 13.00 | 15.00 | 15.00 | 18.00 | 15.00 | 15.00 |
| Alpha Olefin Polymer ($C_{24}$-$C_{28}$) | 7.00 | 5.00 | 7.00 | 5.00 | 3.00 | 3.00 |
| Ethylene/Vinyl Acetate Copolymer (ELVAX 410 Resin) | 0.00 | 0.00 | 0.00 | 0.00 | 2.00 | 3.00 |
| Viscosity @ 55° C., 0.5 1/sec | 5310 | 13,200 | 20,630 | 171,700 | 12,010 | 236,200 |
| Viscosity @ 60° C., 0.5 1/sec | 1180 | 595 | 814 | 1153 | 2663 | 1427 |

TABLE 3

| Component | A Wt. % | B Wt. % | C Wt. % | D Wt. % |
|---|---|---|---|---|
| Petrolatum | 81.00 | 75.00 | 80.00 | 80.00 |
| Ethylene/Vinyl Acetate Copolymer (ELVAX 410 Resin) | 0.00 | 0.00 | 2.00 | 2.00 |
| Polyethylene and Ethylene/Vinyl Acetate Copolymer | 12.00 | 10.00 | 15.00 | 15.00 |
| Hydrogenated Cottonseed Oil | 0.00 | 15.00 | 3.00 | 0.00 |
| Viscosity @ 55° C., 0.5 1/sec | 3184 | 1591 | 18,430 | 8591 |
| Viscosity @ 60° C., 0.5 1/sec | 169 | 44 | 1846 | 1105 |

TABLE 4

| Component | A Wt. % | B Wt. % | C Wt. % | D Wt. % | E Wt. % | F Wt. % |
|---|---|---|---|---|---|---|
| Mineral Oil | 54.8 | 49.8 | 44.8 | 33.5 | 44.9 | 44.9 |
| Mineral Oil and Styrene (Versagel M-750) | 5 | 10 | 15 | 30 | 14.9 | 14.9 |
| Stearyl Alcohol | 18 | 18 | 18 | 18 | 9 | 27 |
| Microcrystalline Wax | 0 | 0 | 0 | 0 | 13.5 | 4.5 |
| Isopropyl Palmitate | 3 | 3 | 3 | 3 | 0 | 0 |
| Dimethicone 200 (Dow) | 1 | 1 | 1 | 1 | 0 | 0 |
| Alkyl Silicone Wax (Stearyl Dimethicone) | 0 | 0 | 0 | 0 | 4 | 4 |
| Aloe Vera | 0.1 | 0.1 | 0.1 | 0 | 0.1 | 0.1 |
| Vitamin E Acetate | 0.1 | 0.1 | 0.1 | 0 | 0.1 | 0.1 |
| Viscosity @ 55° C., 0.5 1/sec | 23 | 33 | 20.5 | Not Done | 126 | 92 |
| Viscosity @ 60° C., 0.5 1/sec | 17.5 | 27 | 17 | Not Done | 77 | 58 |

TABLE 5

| Component | A Wt. % | B Wt. % |
|---|---|---|
| Petrolatum | 80 | 77 |
| Ethylene/Vinyl Acetate Copolymer with Polyethylene | 10 | 10 |
| Alpha Olefin Polymer ($C_{24}$-$C_{28}$) | 7 | 7 |
| Fumed Silica | 3 | 3 |
| Polyisobutene | 0 | 3 |
| Viscosity @ 55° C., 0.5 1/sec | 10,175 | 12,025 |
| Viscosity @ 60° C., 0.5 1/sec | 10,945 | 12,950 |

TABLE 6

| Component | A Wt. % | B Wt. % | C Wt. % |
|---|---|---|---|
| Petrolatum | 75 | 0 | 0 |
| Versagel PT200 (Petrolatum and styrene copolymer) | 0 | 80 | 75 |
| Ethylene/Vinyl Acetate Copolymer and Polyethylene | 10 | 0 | 10 |
| Stearyl Behenate | 15 | 20 | 15 |
| Viscosity @ 55° C. | <50 | 7622 | 3130 |
| Viscosity @ 60° C. | <50 | 7078 | 2593 |

In view of the above, it will be seen that the several objects of the invention are achieved. As various changes could be made in the above-described tissue products without departing from the scope of the invention, it is intended that all matter contained in the above description be interpreted as illustrative and not in a limiting sense.

What is claimed is:

1. A topical ointment comprising from about 30% by total weight of the ointment to about 80% by total weight of the ointment of an emollient, from about 20% by total weight of the ointment to about 40% by total weight of the ointment of a structurant, from about 0.1% by total weight of the ointment to about 40% by total weight of the ointment of a rheology enhancer, from about 0.1% by total weight of the ointment to about 10% by total weight of the ointment of a surfactant having an HLB in the range of from about 2 to about 7, wherein the rheology enhancer is selected from the group consisting of polyisobutylene; hydrogenated polyisobutene and butylene/ethylene/styrene copolymers; hydrogenated polyisobutene and ethylene/propylene/styrene copolymers and butylene/ethylene/styrene copolymers; isononyl isononanoate and ethylene/propylene/styrene copolymers and butylene/ethylene/styrene copolymers; isododecane and ethylene/propylene/styrene copolymers and butylene/ethylene/styrene copolymers; isohexadecane and ethylene/propylene/styrene copolymers and butylene/ethylene/styrene copolymers; isopropyl palmitate and ethylene/propylene/styrene copolymers and butylene/ethylene/styrene copolymers; and combinations thereof.

2. The topical ointment as set forth in claim 1 wherein the surfactant is selected from the group consisting of sorbitan monooleate, sorbitan sequioleate, sorbitan trioleate, glyceryl stearate, sorbitan stearate, sorbitan tristearate, and mixtures thereof.

3. The topical ointment as set forth in claim 1 further comprising from about 0.1% by total weight of the ointment to about 10% by total weight of the ointment of a hydrophilic skin care active.

4. The topical ointment as set forth in claim 3 wherein the hydrophilic skin care active is selected from the group consisting of botanicals, glycerin, hydrogenated starch hydrolysate, propylene glycol, sodium PCA, sodium lactate, sorbitol, and mixtures thereof.

5. A topical ointment comprising from about 30% by total weight of the ointment to about 80% by total weight of the ointment of an emollient, from about 20% by total weight of the ointment to about 40% by total weight of the ointment of a structurant, from about 0.1% by total weight of the ointment to about 40% by total weight of the ointment of a rheology enhancer, from about 0.1% by total weight of the ointment to about 10% by total weight of the ointment of a particulate material, and from about 0.1% by total weight of the ointment to about 10% by total weight of the ointment of a low HLB surfactant, wherein the rheology enhancer is selected from the group consisting of polyisobutylene; hydrogenated polyisobutene and butylene/ethylene/styrene copolymers; hydrogenated polyisobutene and ethylene/propylene/styrene copolymers and butylene/ethylene/styrene copolymers; isononyl isononanoate and ethylene/propylene/styrene copolymers and butylene/ethylene/styrene copolymers; isododecane and ethylene/propylene/styrene copolymers and butylene/ethylene/styrene copolymers; isohexadecane and ethylene/propylene/styrene copolymers and butylene/ethylene/styrene copolymers; isopropyl palmitate and ethylene/propylene/styrene copolymers and butylene/ethylene/styrene copolymers; and combinations thereof.

6. The topical ointment as set forth in claim 5 wherein the rheology enhancer is polyisobutylene.